(12) United States Patent
Stickley

(10) Patent No.: US 7,360,625 B2
(45) Date of Patent: Apr. 22, 2008

(54) WEARABLE STETHOSCOPE SANITIZING DEVICE

(76) Inventor: Robert F. Stickley, 3309 Country Meadow Dr., Christiansburg, VA (US) 24073

( * ) Notice: Subject to any disclaimer, the term of this patent is extended or adjusted under 35 U.S.C. 154(b) by 11 days.

(21) Appl. No.: 11/544,692

(22) Filed: Oct. 6, 2006

(65) Prior Publication Data
US 2007/0080017 A1    Apr. 12, 2007

Related U.S. Application Data

(60) Provisional application No. 60/723,975, filed on Oct. 6, 2005.

(51) Int. Cl.
*A61B 7/02* (2006.01)
*A61L 2/18* (2006.01)
*A61L 2/00* (2006.01)

(52) U.S. Cl. .................. 181/131; 422/300; 422/28

(58) Field of Classification Search ........... 181/131; 422/300, 28, 292; 134/200; 239/274
See application file for complete search history.

(56) References Cited

U.S. PATENT DOCUMENTS

| | | | | |
|---|---|---|---|---|
| 3,530,261 | A * | 9/1970 | Guim ................ | 379/452 |
| 5,641,464 | A * | 6/1997 | Briggs et al. ........ | 422/300 |
| 5,722,537 | A * | 3/1998 | Sigler ................ | 206/205 |
| 5,892,233 | A * | 4/1999 | Clement ............ | 250/455.11 |
| 6,018,835 | A * | 2/2000 | Schonfeld .......... | 15/97.1 |
| 7,282,177 | B2 * | 10/2007 | Castaneda .......... | 422/28 |
| 7,282,186 | B2 * | 10/2007 | Lake et al. ......... | 422/300 |
| 2002/0146343 | A1 * | 10/2002 | Jenkins et al. ....... | 422/24 |
| 2005/0236579 | A1 * | 10/2005 | Jenkins et al. ...... | 250/455.11 |
| 2006/0213920 | A1 * | 9/2006 | Agarwal et al. ...... | 221/45 |
| 2007/0256753 | A1 * | 11/2007 | Riley ................ | 141/69 |

OTHER PUBLICATIONS

"Ultra-Clean Stethoscope Sterilizer", http://www.uvs-ultraclean.com/stethoscope.htm, no date provided.*

* cited by examiner

*Primary Examiner*—Edgardo San Martin
(74) *Attorney, Agent, or Firm*—Jeffrey K. Seto

(57) ABSTRACT

A small, lightweight sanitizing device that is adapted for attachment to a stethoscope. When the stethoscope is not being used the device covers the diaphragm and bell portions of the stethoscope with sanitizing pads that kill germs and prevent the spread of disease between patients that are examined with the stethoscope. When the health care provider needs to use the stethoscope, the device can be slid up a length of the stethoscope to a desired location so that the diaphragm is exposed for use. The device is advantageously produced with a narrow top that frictionally engages with the tube of the stethoscope so that the sanitizing device stays at the desired location until the user pulls the device back down over the diaphragm. The present sanitizing device can be used with both adult and pediatric stethoscopes. In an alternative embodiment, the sanitizing device is designed to be held within the front pocket of a health care provider's shirt or lab coat so that sterilization of the diaphragm and bell are achieved by simply placing the head portion of the stethoscope in the front pocket.

20 Claims, 6 Drawing Sheets

WEARABLE STETHOSCOPE SANITIZING DEVICE

BACKGROUND OF THE INVENTION

The present invention was originally disclosed in U.S. provisional patent application Ser. No. 60/723,975 filed on Oct. 6, 2005, and priority is claimed to the provisional application.

The present invention relates generally to the field of sanitizing devices and more specifically to an omni-present device for sanitizing stethoscopes.

Stethoscopes are used every day by nurses and doctors around the world to listen to sounds that are produced within the human body. A traditional stethoscope consists of a head portion for collecting sounds, one or two sound tubes that transport the sounds and two ear-pieces that fit inside the ears of the user. The head portion includes a large diaphragm opposed to a smaller bell. The diaphragm or the bell is pressed against the skin of a patient to collect high or low frequency sounds. The sound tubes connect the head portion to the ear-pieces. Since stethoscopes generally are not disposable, the same diaphragm will be pressed against the skin of many different patients. In order to prevent the transfer of any harmful germs between patients, stethoscope diaphragms should be sanitized after every use. Stethoscope cleaning, however, is often a forgotten practice among medical personnel. One study found that a majority of health care providers cleaned their stethoscopes every month at the most. Another study showed that most health care providers knew that cleaning their stethoscope was important, yet 38% of them had never cleaned their stethoscopes. By not cleaning the diaphragms, stethoscopes become a vector for the spread of nosocomial diseases (diseases acquired while in the hospital). This is especially troublesome because many patients in hospitals already have a weakened immune system. In a third study of 150 health care workers, staphylococcus (staph) species were cultured from 89% of the participants' stethoscopes. Nosocomial diseases kill an estimated 103,000 people in the United States a year, and the danger is worsening as many hospital infections can no longer be easily cured with common antibiotics. One of the deadliest germs is Methicillin-Resistant Staphylococcus Aureus (MRSA), which may live harmlessly on the skin but causes havoc when it enters the body. Patients that do survive MRSA may spend weeks or months in the hospital and endure several operations to cut out infected tissue. In 1974, 2% of staph infections were from MRSA. By 1995, that number had risen to 22%. Today, experts estimate that more than 60% of staph infections are MRSA. Hospitals in Denmark and Finland once faced similar infection rates, but were able to bring them down to below 1% through rigorous enforcement of sanitation rules that included hand washing and the cleaning of rooms and equipment. Studies suggest that a 70% alcohol solution will kill 95% to 98% of bacteria on surfaces. It has been shown that a simple cleansing of a stethoscope diaphragm with an alcohol swab will reduce the bacteria count by 94% or more.

What is needed in the field is a sanitizing device that is easy to use and small enough to be attached to a stethoscope without adding unmanageable weight or bulk. Having the sanitizing device attached to the stethoscope would automatically remind the health care worker to sanitize the diaphragm after each use. The ideal device would include an alcohol solution and require very little effort to use in sanitizing the diaphragm of the stethoscope.

SUMMARY OF THE INVENTION

A small and lightweight sanitizing device that is adapted for attachment to a stethoscope. The sanitizing device covers the head of the stethoscope when the stethoscope is not being used and when the stethoscope is needed for use, the device can be slid up the sound tube of the stethoscope thereby exposing the head. The sanitizing device comprises a back panel, a front panel and an attachment mechanism. The back panel has a narrow top, a wide bottom and an interior surface, wherein a layer of absorbent material that is adapted for holding a sanitizing agent is attached to the interior surface. The front panel has the same general shape and size as the back panel. The right side of the front panel is connected to the left side of the back panel and when the front panel is folded over the back panel an interior space is created that is large enough to house the diaphragm. The attachment mechanism is used to temporarily attach the free sides of the front and back panels. When the panels are attached via the attachment mechanism, the sanitizing device takes on a cone-like shape and when the device is slid down over the head, the absorbent material with the sanitizing agent comes into contact with the diaphragm.

In one embodiment, the back panel and the front panel are both made of a flexible material, and a second layer of absorbent material that is adapted for holding the sanitizing agent is also attached to the interior surface of the front panel. This allows for sanitizing of both the diaphragm and the bell no matter which direction the head faces when it is slid into the sanitizing device. The narrow open top of the device prevents the head of the stethoscope from exiting through the top of the device, and the wide, open bottom of the device allows the head of the stethoscope to be easily slid into, and out of, the interior of the sanitizing device. The narrow tops of the panels form a frictional seal with the tube of the stethoscope so that when the device is slid up a length of the tube to a desired location, the device stays at the desired location until the device is slid back down over the head by the user. The layers of absorbent material, which hold the alcohol gel, have surface areas that are greater than the surface areas of the diaphragm and the bell so that the absorbent materials completely cover the diaphragm and bell when the head of the stethoscope is housed within the sanitizing device.

The sanitizing pads can be attached to the panels of the present device by Velcro®, clips, adhesives, or the pads can be slid into slots provided in the bottom of the back panel. When clips are used the sanitizing pads include a rigid or semi-rigid backing that aids in keeping the pads in place. When the slot method is used to attach a pad to the panel, the interior surface of the back panel includes a frame through which the majority of the sanitizing pad is exposed so that the pad can make contact with the diaphragm.

In an alternative embodiment, the device includes a rigid or semi-rigid front cover that fits over a rigid back piece. The back piece has an "H" shaped cross-section wherein the horizontal cross bar of the back piece is purposely offset with respect to the sides. This offset allows a large stethoscope head to be housed within one side of the device and a smaller head to be housed within the opposite side of the device.

It is an object of the present invention to provide a stethoscope sanitizing device that is always attached to the stethoscope so that the health care worker is always reminded to sanitize the head portion after each use.

It is another object of the present invention to provide a stethoscope sanitizing device that cleans both the bell and the diaphragm surfaces of the stethoscope.

It is yet another object of the present invention to provide a stethoscope sanitizing device that can be used with stethoscopes of varying sizes including adult and pediatric stethoscopes.

It is still another object of the present invention to provide a sanitizing device that requires little effort by the user to sanitize the head of a stethoscope.

BRIEF DESCRIPTION OF THE DRAWINGS

The invention of the present application will be described in detail with reference to the accompanying drawing(s), given only by way of example, in which.

DETAILED DESCRIPTION OF THE INVENTION

Figure 1A:
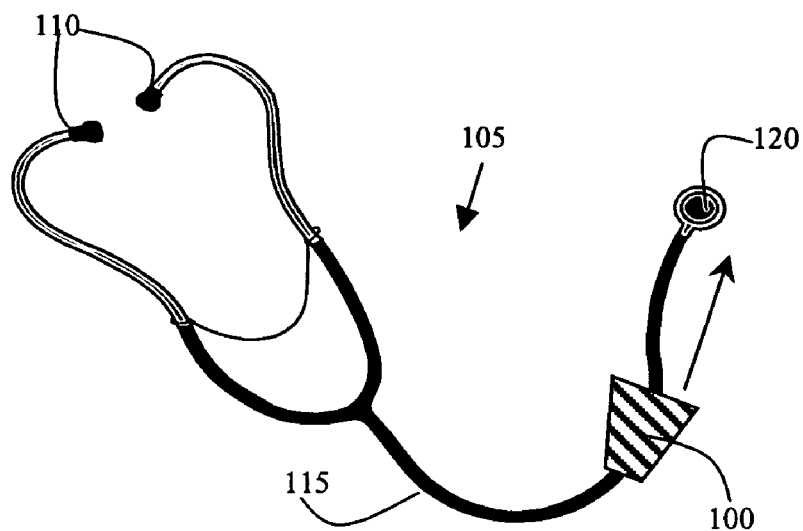
FIG. 1(a) shows the preferred embodiment attached to a stethoscope.

FIG. 1(a) shows the preferred embodiment 100 slide-ably attached to the sound conveying tube 115 of a stethoscope 105. During the normal use of the stethoscope 105, a nurse or doctor presses the diaphragm or the bell in the head 120 against various areas on a patient's body and listens, via ear-pieces 110, to the sounds of the patient's body. The preferred embodiment 100 is a flexible cone shaped pocket that uses foam pads to store a sanitizing agent, such as alcohol gel, in its interior. The cone shaped pocket has a large opening at one end that allows for entry of the head 120, and a small opening at the opposite end that allows the present sanitizing device 100 to be slid along tube 115. After the nurse or doctor is finished using the stethoscope 105, the sanitizing device 100 is slid down the length of tube 115 until it completely covers the head 120, as is shown in FIG. 1(b).

Figure 1B:
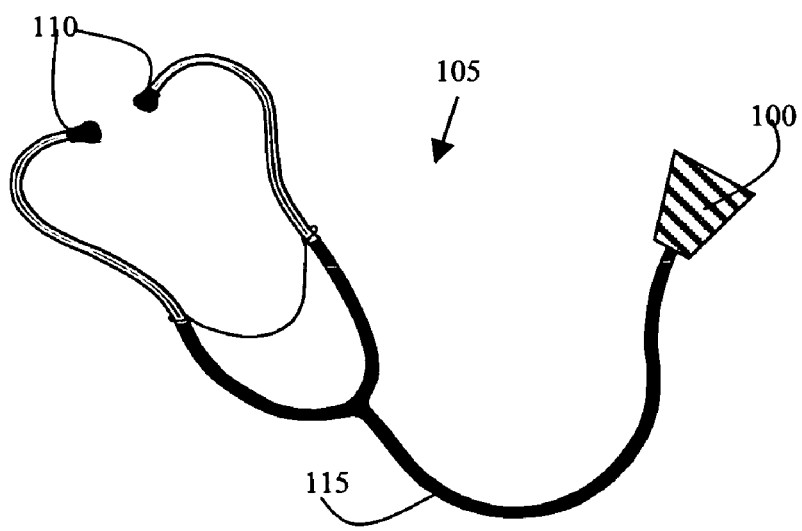
FIG. 1(b) shows the preferred embodiment in operational position.

FIG. 1(b) shows the preferred embodiment 100 in operational position, covering the head portion of stethoscope 105. The operational position is also called the sanitizing position, because in that position the foam pads and sanitizing agent inside the preferred embodiment 100 initiate and maintain contact with the stethoscope's diaphragm and bell, thereby sanitizing the diaphragm and bell, and minimizing any cross contamination. The germ killing ability of the present device 100 can be increased via simple massaging of the device 100 while the head is inside the device.

Figure 2:
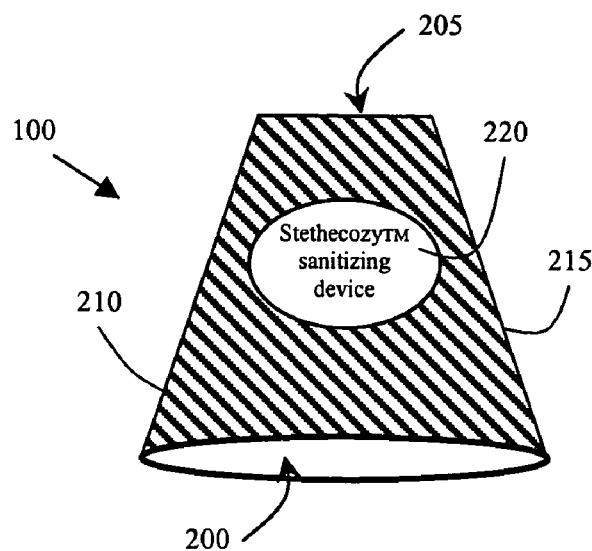
FIG. 2 is a perspective view of the preferred embodiment.

FIG. 2 is a perspective view of the preferred embodiment 100, showing the large opening 200 in the bottom of the device and indicating the small opening 205 in the top of the device. The size of the small opening 205 is large enough to allow passage therethrough of the stethoscope's sound tube. However, it is also small enough to create a small amount of friction with the. sound tube. This small amount of friction allows the device 100 to stay at any location along the sound tube that the device is placed by the user. The left side 210 of the preferred sanitizing device 100 is permanently sealed. However, the right side 215 of the device is release-ably attached. By opening the right side 215 of the device, the user can gain access to the interior pads in order to add sanitizing agent or replace the pads. An advertisement 220 may optionally be provided on the present Stethecozy™ sanitizing device to let patients know that the stethoscope has been sanitized after every use, and to give the patients some peace of mind. The advertisement 220 could also be used to promote other products.

Figure 3:
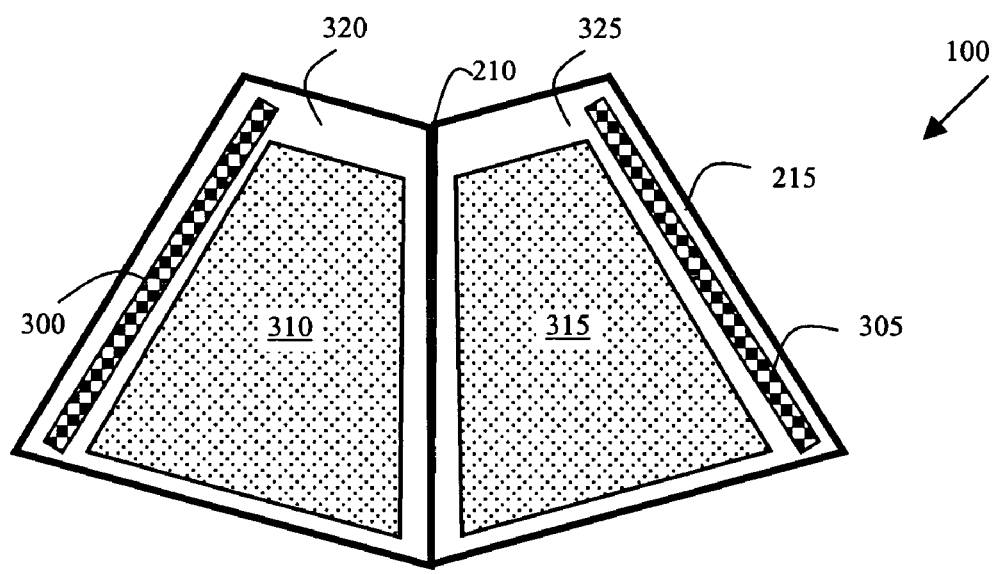
FIG. 3 shows the interior of the preferred embodiment.

FIG. 3 shows the interior of the preferred embodiment 100, which is constructed of two pieces 320 & 325 of backed vinyl that are permanently joined along the length of one side 210. The present sanitizing device could also be constructed from one piece of material that is folded in half, as long as the balance of flexibility and stiffness of the material is appropriate. The back piece 325 may also be rigid or semi-rigid and the front piece 320 made larger than the back in order to create and maintain an opening in the bottom of the device when the opposite sides of the two pieces are attached. This is important because the Stethecozy™ must remain open in order to accept the stethoscope's head when it is pulled down in the sanitizing position. Materials other than vinyl could also be used to construct the exterior of the present device, but they must by able to resist penetration of the sanitizing agent. Alternative materials must also possess the balance of flexibility and stiffness to allow for easy use and occasional massaging of the diaphragm and bell through the Stethecozy™ to assist in cleaning. Alternative exterior material should also be hypoallergenic to avoid patient sensitivities. Decorative fabrics and textures could also be incorporated into the manufacturing of the present device. After permanent joining of side 210, the necessary semi-cone shape of the device is created by temporarily joining the opposite sides of the two exterior pieces 320 & 325 of vinyl. Velcro® strips 300 & 305 are used to temporarily hold the pieces together. Of course, other closure devices, including snaps, tabs and zip-locks, can be used in alternative embodiments. The present sanitizing device can be provided in multiple sizes to fit all sizes of stethoscopes and easily modified for use with electronic stethoscopes.

In the preferred embodiment 100, the two foam pieces 310 & 315 are attached to the insides of the vinyl pieces 320 & 325 with an adhesive. Each foam pad 310 & 315 includes a backing that prevents the sanitizing agent from degrading the adhesive. A bracket, or frame, could also be permanently attached to the insides of the vinyl pieces and removable foam pads could be used. Alternatively straps or clips attached to the insides of the vinyl pieces could be used to temporarily hold the foam pads. Replacement foam pads would be provided with the alternative embodiments. Of course, inexpensive materials could be used during construction and the entire sanitizing device could be disposable, and replaced after a specified period.

The preferred sanitizing agent is alcohol gel. Alcohol gel is already on the market and readily available at most hospitals. It is also likely that alcohol gel will not cause any unwanted skin reactions. Other sanitizing agents could also be used in other embodiments.

An important aspect of the present invention is that it is always attached to the medical device that it's intended to sanitize, so the user will always be reminded to use it. The ease of use is another important feature. Most germs on the diaphragm and bell are killed by simply sliding the Stethecozy™ over the head of the stethoscope. Simple massaging of the sanitizing device while in its operational position raises the level of sanitation provided.

Figure 4:
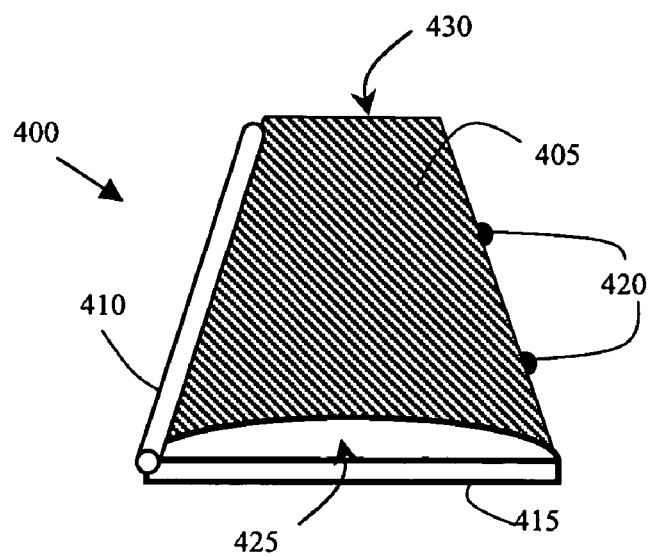
FIG. 4 is a perspective view of an alternative embodiment.

FIG. 4 shows an alternative embodiment 400 of the present sanitizing device. This embodiment 400 works in the same manner as the preferred embodiment wherein the head of the stethoscope enters and exits the sanitizing device 400 via a large opening 425 in the bottom of the device, and the small opening 430 at the top of the device is adapted to slide along the tube of stethoscope. The alternative embodiment 400 differs from the preferred embodiment by incorporating a reversible feature to the device, which allows the same sanitizing device to be used with both adult sized and pediatric sized stethoscopes. The back panel 415 of the device 400 is made of a rigid, or semi-rigid, material that allows both sides of the panel 415 to be selectively used to hold a sanitizing foam pad. The front panel 405 is attached to one side of the back panel 415 via a hinge 410 that allows the front panel 405 to swing so that the front panel can be used to cover either the front or the back side of the rigid back panel 415. No matter which side the front panel 405 covers, the front panel is secured in place by snapping over studs 420 that are permanently attached to the opposite side of the back panel 415.

Figure 5:
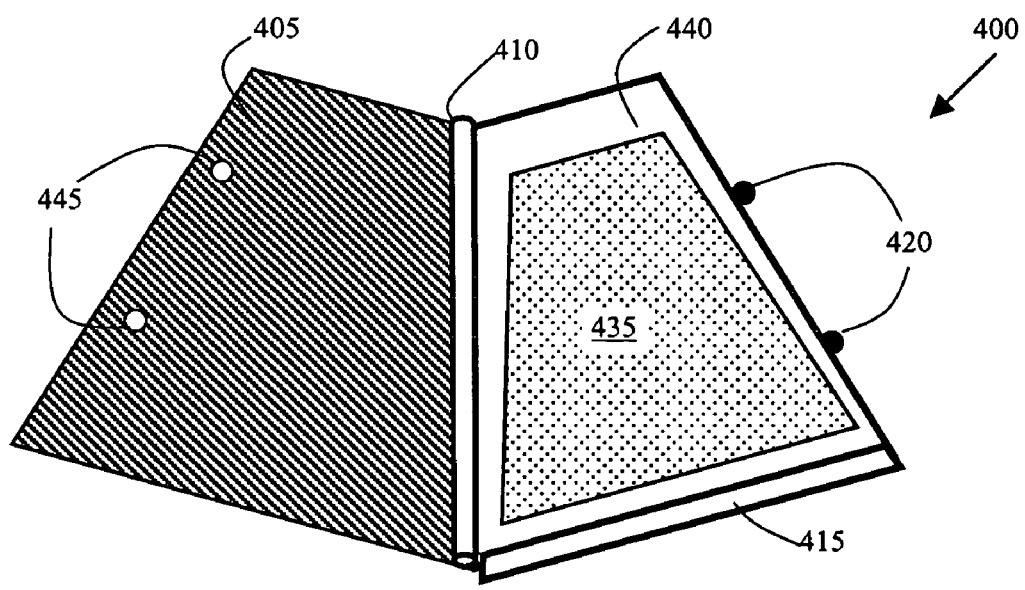
FIG. 5 shows the alternative embodiment in the open position.

FIG. 5 shows the alternative embodiment 400 in the open position. To open this sanitizing device 400, the front panel 405 is pulled away so that the holes 445 in the front panel are released from the studs 420 on the side of the back panel 415. The front side of the back panel 415 includes a window frame like structure 440 that holds an adult sized sanitizing pad 435 in place. The adult sized sanitizing pad 435 can be slid into and out of the back panel 415 through an opening, or slot, in the bottom of the back panel 415.

Figure 6:
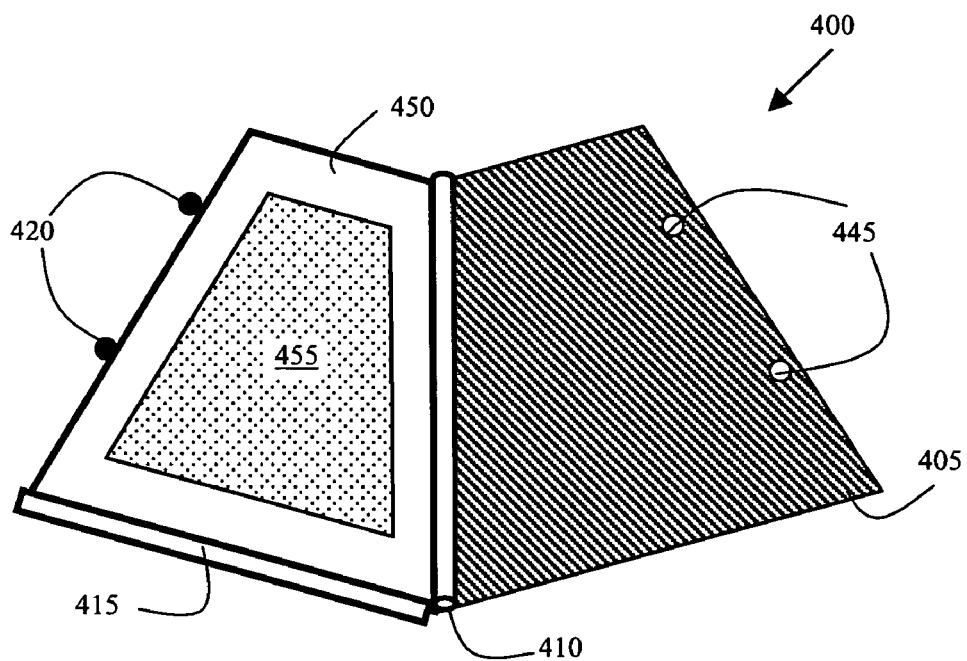
FIG. 6 shows the back of the alternative embodiment.

FIG. 6 shows the reverse side, or back, of the alternative embodiment 400. The reverse side of the back panel 415 includes another window frame like structure 450 that is designed to hold a smaller, pediatric sized sanitizing pad 455. When the device 400 is being used to sanitize pediatric stethoscopes, the adult sized pad on the opposite side of the back panel can be removed to prevent unwanted dispersal of the sanitizing gel. To close the front panel 405, the panel is rotated via hinge 410 over the pediatric pad 455 and the holes 445 in the front panel 405 are snapped in place over the studs 420 on the side of the back panel 415.

Figure 7:
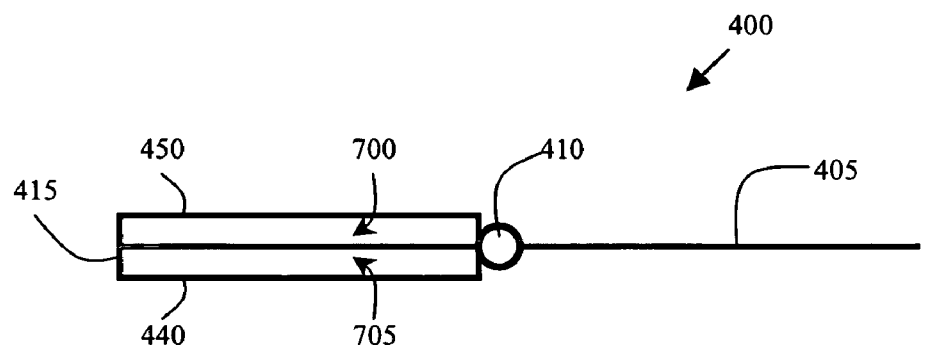
FIG. 7 is a bottom view of the alternative embodiment.

FIG. 7 is a bottom view of the alternative embodiment 400. The bottom of the rigid back panel 415 includes two opening 700 & 705 for insertion of the pediatric and adult sized pads respectively. When a pediatric sized sanitizing pad is inserted into opening 700, the majority of the pad will be exposed through window frame 450 and the device 400 can be used to sanitize a pediatric diaphragm. When an adult sized sanitizing pad is inserted into opening 705, the majority of the pad will be exposed through window frame 440 and the device 400 can be used to sanitize an adult sized diaphragm. The front panel 405 can be used to cover either side of the back panel 415, via hinge 410, depending on the needs of the user.

Figure 8:
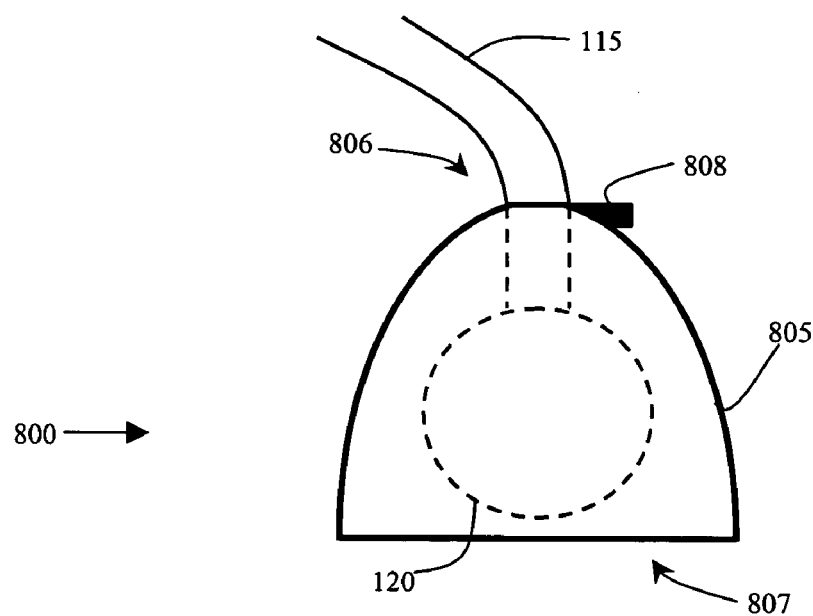
FIG. 8 is a frontal view of a second alternative embodiment in operational position.

FIG. 8 is a frontal view of a second alternative embodiment 800 of the present sanitizing device in operational position. This embodiment 800 is also used in a similar manner as the preferred embodiment, with the head 120 of the stethoscope entering and exiting through the large open bottom 807 of the device 800. This embodiment 800 also includes a narrow open top 806 that is designed to frictionally engage with the tube 115 of the stethoscope so that sanitizing device 800 will stay at a desired position on the tube 115 when the device is slid up the tube by a user. To assist in holding the device 800 on the sound tube 115 when the device is slid a length of the tube, a holding button 808 can be provided at the top of the device. The holding button 808 is slide-ably attached to the device 800 so that when pushed in, the inside of the button 808 presses against the sound tube 115 and frictionally engages with the tube. The holding button 808 can be biased so that a second push will release pressure from the sound tube 115, or the button 808 may include a catch that holds the button in the "in" position and the button must be pulled outward to release pressure on the sound tube.

Figure 9:
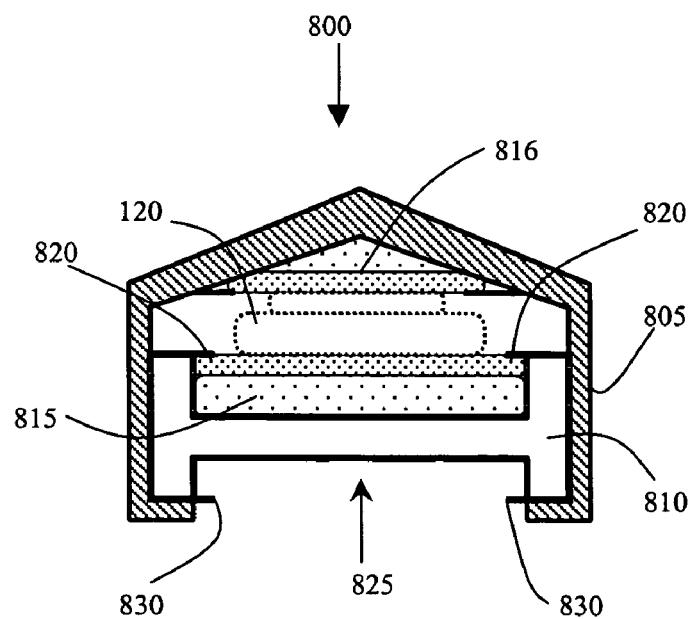
FIG. 9 is a cross-sectional bottom view of the second alternative embodiment.

FIG. 9 is a cross-sectional bottom view of the second alternative embodiment 800. In this embodiment 800, the front cover 805 is made of a semi-rigid material and the back panel 810 is made of rigid material. This construction allows the front cover 805 to be removed from the back panel 810 by pulling on one of the back edges of the front cover 805. Alternatively, the front cover 805 may also be made of a rigid material, in which case the front cover could be removed from the back panel 810 by sliding the cover up and off of the top of the back panel, or by pulling the cover out of recesses that are provided on the back panel. This embodiment 800 also includes the reversible feature that allows the sanitizing device to be used with both adult sized and pediatric sized stethoscopes. FIG. 9 is shown with the diaphragm sanitizing pad 815 in place on the adult side of the device, i.e., the side for housing an adult sized stethoscope head. The sanitizing pad 815 is snapped into position and held in place be clips 820 that are provided on the sides of the back panel 810. The diaphragm sanitizing pad 815 is designed to make contact with and clean the diaphragm portion of stethoscope's head 120. A second sterilizing pad 816 is provided inside the cover 805 to make contact with and clean the bell portion of the stethoscope's head 120. The second pad 816 is also preferably snapped into position and held in place by clips that are provided on the inside the cover 805. Sufficient room is provided between the diaphragm sanitizing pad 815 and the second pad 816 for entry and exit of the adult sized head 120 of the stethoscope. When the health care worker wishes to use the sanitizing device 800 with a pediatric sized stethoscope, the diaphragm sanitizing pad 815 is removed from the back panel 810 and snapped into place in opening 825. The diaphragm sanitizing pad is held in place by clips 830 that are provided on the opposite side of the back panel 810. The cover 805 is removed from the adult side of the back panel 810 and placed over the pediatric side of the back panel. When the front cover 805 is placed over the pediatric side of the back panel 810 the interior space provided between the pediatric pad and the pad 816 in the front cover is reduced so that the thinner pediatric diaphragm and bell make contact with the sanitizing pads. To effect the change in interior space that is provided on the adult and pediatric sides, when the cover 805 is attached, the crossbar of the back panel 810 (or the horizontal portion of the "H" shaped cross-section) is intentionally off-set so that it is closer to the pediatric side of the back panel 810. Each sanitizing pad is preferably made of at least two layers of material, with the bottom layer acting as a reservoir for holding an amount of sanitizing gel and the top layer of the pad acting as a dispersal layer that slowly secretes just enough sanitizing gel to sanitize the diaphragm and bell. A third, rigid layer may also be provided in the sanitizing pad, under the bottom reservoir layer, to help contain the sanitizing gel.

Figure 10:
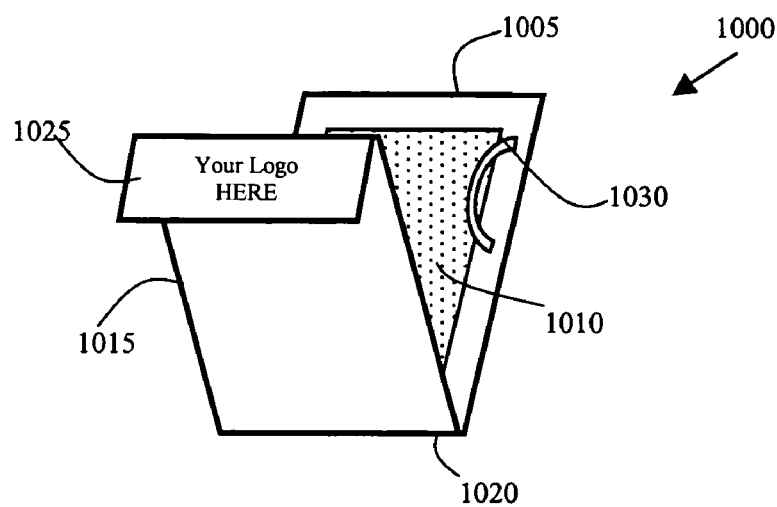
FIG. 10 is a perspective view a third alternative embodiment.

FIG. 10 is a perspective view of a third alternative embodiment 1000 of the present stethoscope sanitizing device. This embodiment 1000 is designed to fit into the front pocket of a health care provider's shirt or lab coat, and takes advantage of the carry method used by many doctors and nurses, wherein the stethoscope is slung around the person's neck. When in its operational position, this embodiment 1000 provides sanitation of the diaphragm and bell by simply sticking the head portion of the stethoscope into the person's front pocket. The sanitizing device 1000 can be made of a single sheet of material that has a similar width as a traditional front pocket and has a length that is approximately twice as long as the front pocket. The material is folded substantially in half so that it obtains the size of the front pocket, and front and back panels are created. Of course, the device 1000 can also be created by attaching the bottoms of two different sheets of material. In either case, a back panel 1005, a front panel 1015 and a bottom 1020 of the device are created. The back panel 1005 includes a sanitizing pad 1010 that is preferably attached to the back panel with Velcro®, however, other attachment methods including adhesives, straps and rigid clips may also be used. As with the second alternative embodiment (shown in FIGS. 8 & 9), the sanitizing pad 1010 preferably includes more than one layer of material. The multiple layers aid in containing and dispersing the sanitizing gel, and also prevent the sanitizing gel from interfering with attachment of the pad 1010 to the back panel 1005. The front panel 1015 also preferably includes a second sanitizing pad that is attached to the front panel's interior side, so that both the diaphragm and the bell of the stethoscope's head are sanitized. The front panel 1015 may also be provided with flap 1025 that is designed to hang over, and outside of, the front pocket. This flap 1025 will prevent the device 1000 from sliding too far down front pockets that are extremely deep. The flap 1025 can also display a logo that lets others know that the health care worker is using the sanitizing device 1000, which will give patients peace of mind knowing that they are being examined with a sterile stethoscope. The back panel 1005 may also include a spring clip 1030 that maintains a slight opening between the two panels 1005 & 1015, to assist in insertion of the stethoscope head into the sanitizing device 1000. The spring clip 1030 intentionally has a height that is less than that of the stethoscope's head so that the clip does not interfere with the head making contact with the sanitizing pads. Of course, more than one spring clip may be provided and the clip(s) may be attached to the front panel, rather than to the back panel as shown. The clips may also be included within the construction of the front or back panel to allow easy, unobstructed placement of the head of the stethoscope within the device.

Figure 11:
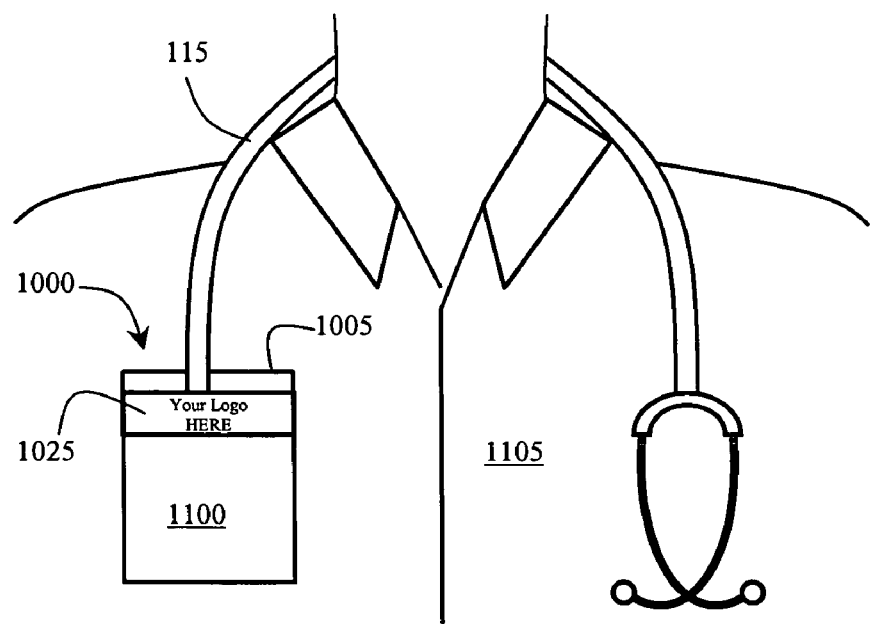
FIG. 11 is a frontal view of the third alternative embodiment in operational position.

FIG. 11 shows the third alternative embodiment 1000 in its operational position, within the front pocket 1100 of a health care provider's shirt or coat 1105. When the stethoscope's tube 115 is slung around the person's neck, the head of the stethoscope is easily placed within the interior of the sanitizing device 1000. The one or more spring clips provided inside the sanitizing device 1000 facilitate entry of the head into the interior of the device. The back panel 1005 of the device 1000 can be made slightly higher than the front panel to further facilitate entry of the head into the interior of the sanitizing device 1000. The front flap 1025 of the sanitizing device 1000 hangs over the top edge of the pocket 1100 and also assists in placing the stethoscope's diaphragm into the interior of the sanitizing device 1000.

The foregoing description of the specific embodiments will so fully reveal the general nature of the invention that others can, by applying current knowledge, readily modify and/or adapt for various applications such specific embodiments without departing from the generic concept. For example, the present sanitizing device could be produced in a shape other than a cone, such as a heart or round for a smiley face, and still perform its intended use. The only limitations being that the bottom of the device allow entry of the stethoscope's diaphragm, and a small opening that is complementary in size to the stethoscope's tube be provided at the top of the device. Therefore, such adaptations and modifications should and are intended to be comprehended within the meaning and range of equivalents of the disclosed embodiments. It is to be understood that the phraseology of terminology employed herein is for the purpose of description and not of limitation.

I claim:

1. A sanitizing device that is adapted for attachment to a stethoscope, wherein the device covers a head of the stethoscope when the stethoscope is not being used and the device can be slid up a tube of the stethoscope when the stethoscope is being used, the sanitizing device comprising:

a back panel, the back panel having a narrow top, a wide bottom, a left side, a right side and an interior surface, wherein a layer of absorbent material that is adapted for holding a sanitizing agent is attached to the interior surface;

a front panel, the front panel also having a narrow top, a wide bottom, a left side, and a right side, wherein the right side of the front panel is connected to the left side of the back panel; and, an attachment mechanism, wherein the attachment mechanism is able to temporarily attach the left side of the front panel to the right side of the back panel when the front panel is folded over onto the back panel so that the sanitizing device takes on a cone-like shape and an interior of the device is created that is large enough to accomodate the head of the stethoscope and, when the device is slid down over the diaphragm, the layer of absorbent material comes into contact with a diaphragm of the head of the stethoscope.

2. The device of claim 1, wherein the back panel is made of a semi-rigid material the front panel is made of flexible material, and a second layer of absorbent material that is adapted for holding the sanitizing agent is attached to an interior of the front panel so that sanitizing of the diaphragm and a bell of the head are provided by the device.

3. The device of claim 1, wherein the narrow tops of both panels have a width that is smaller than a width of the head of the stethoscope thereby preventing the head from sliding out of a top of the device, and the wide bottoms of both panels have a width that is greater than the width of the head so that the head can be easily slid into, and out of, the interior of the device via a bottom of the device.

4. The device of claim 1, wherein the narrow tops of the panels form a frictional seal with the tube of the stethoscope when the panels are attached via the attachment mechanism so that when the device is slid up a length of the tube to a desired position, the device stays at the desired position via the frictional seal until the device is slid back down the length of the tube by a user.

5. The device of claim 1, wherein the layer of absorbent material has a surface area that is greater than a surface area of the diaphragm so that the absorbent material completely covers the diaphragm when the diaphragm is housed within the interior of the device, and wherein the sanitizing agent is an alcohol gel.

6. The device of claim 1, wherein the back panel further comprises at least one slot in the bottom of the back panel into which the layer of absorbent material may be slid into and out of the device, and wherein the interior surface of the back panel includes a frame through which a majority of the absorbent material is exposed so that the absorbent material can make contact with the diaphragm when the diaphragm is slid into the device.

7. The device of claim 6, wherein the back panel includes a layer of rigid material, and the front panel is connected to the back panel by a hinge so that the front panel can cover a front of the back panel and can also be swung around to cover a back of the back panel, and wherein the back panel includes a second slot in the bottom that allows an absorbent pad to be inserted into the device, and the back panel also includes a second frame that allows a majority of the absorbent pad to be exposed out of the back of the back panel.

8. A sanitizing device that is adapted for attachment to a stethoscope, wherein the device covers a head of the stethoscope when the stethoscope is not being used and the device can be slid up a tube of the stethoscope when the stethoscope is being used, the sanitizing device comprising:
a rigid back panel, wherein a front of the back panel houses a first absorbent pad that is adapted for holding an amount of sanitizing agent and the first absorbent pad can be snapped into and out of the back panel via multiple clips that are provided in the back panel; and,
a cover, wherein the cover is able to releasably attach to the front of the back panel so that when the cover is attached, a first interior space is created between the cover and the first absorbent pad that is large enough to house the head.

9. The device of claim 8, wherein the diaphragm is able to enter and exit through an opening in a bottom of the device, and wherein a small opening is provided in a top of the device that allows passage therethrough of a tube of the stethoscope but prevents passage of the head.

10. The device of claim 9, wherein the small opening in the top of the device frictionally engages with the stethoscope's tube in manner that allows the tube to slide through the small opening only when the device is moved by a user, so that when the device is slid up a length of the tube to a desired position, the device remains at the desired position until the user moves the device back to an original position.

11. The device of claim 8, wherein a back of the back panel houses a second absorbent pad that is adapted for holding another amount of sanitizing agent and the second absorbent pad can be snapped into and out of the back panel via a second set of clips in the back of the back panel, and wherein the cover is also able to releasable attach to the back of the back panel so that a second interior space is created between the cover and the second absorbent pad, the second interior space having a volume that is different than the first interior space.

12. The device of claim 8, wherein the cover includes a second absorbent pad that is adapted to hold another amount of sanitizing agent, the second absorbent pad being housed on an interior of the cover so that sanitizing of both sides of the head is provided by the device.

13. The device of claim 11, wherein the first interior space is adapted for housing an adult sized head and the second interior space is adapted for housing a pediatric sized head, and wherein the first absorbent pad and the second absorbent pad each include more than one layer of material.

14. The device of claim 9, wherein the top of the device includes a holding button that when pressed exerts pressure against the tube and allows the device to be held at a desired position along a length of the tube.

15. A sanitizing device that is adapted for insertion into a front pocket of a shirt, a blouse and a coat, wherein the sanitizing device is also adapted to receive a head of a stethoscope, so that a user is able to sanitize the head by inserting the head into the front pocket, the sanitizing device comprising:
a back panel, wherein the back panel houses a first sanitizing pad that is adapted to hold an amount of sanitizing agent and the first sanitizing pad is exposed to an interior of the device;
a front panel, wherein a bottom of the front panel is permanently attached to a bottom of the back panel and wherein the front panel and the back panel both have a same general dimensions as the front pocket; and,
a flap, wherein the flap is permanently attached to a top of the front panel and the flap is adapted to hang over a front of the front pocket.

16. The sanitizing device of claim 15, wherein the front panel houses a second sanitizing pad that is adapted to hold another amount of sanitizing agent, and wherein the second sanitizing pad is exposed to the interior of the device.

17. The sanitizing device of claim 16, wherein the first and second sanitizing pads are replaceable and both pads are also constructed of more than one layer of material.

18. The sanitizing device of claim 15, wherein the back panel has a height that is slightly greater than a height of the front panel, so that insertion of the diaphragm into the interior of the device is facilitated.

19. The sanitizing device of claim 15, wherein the sanitizing agent is an alcohol gel.

20. The sanitizing device of claim 15, further comprising a spring clip that is housed within the interior of the device, the spring clip biasing the device in a semi-open position wherein a separation is maintained between the front and back panels.

* * * * *